United States Patent [19]

Arbuckle

[11] 4,027,608

[45] June 7, 1977

[54] SUTURING DEVICE

[75] Inventor: Norman B. Arbuckle, Costa Mesa, Calif.

[73] Assignee: Raymond Kelder, Newport Beach, Calif. ; a part interest

[22] Filed: Feb. 20, 1976

[21] Appl. No.: 659,743

[52] U.S. Cl. .............................. 112/169; 128/334 R
[51] Int. Cl.² ......................................... D05B 1/00
[58] Field of Search ......... 112/169, 80; 128/334 R, 128/334 C, 335, 339

[56]  References Cited
UNITED STATES PATENTS

| | | | |
|---|---|---|---|
| 2,580,964 | 1/1952 | Skaller | 112/169 |
| 2,945,460 | 7/1960 | Kagiyama | 112/169 |
| 2,988,028 | 6/1961 | Alcamo | 112/169 |

*Primary Examiner*—Werner H. Schroeder
*Assistant Examiner*—Peter Nerbun
*Attorney, Agent, or Firm*—Harvey C. Nienow

[57] ABSTRACT

A suturing device for sewing animal skin or flesh having a reversely movable arcuate needle and a pivotal rocker arm, said needle and rocker arm being movable in planes at substantially right angles to each other whereby said rocker arm affords a loop in the suturing thread for each succeeding stitch afforded by the needle. When operating, the device includes a continually operating electric motor having clutch means for engaging and disengaging, as desired, a drive shaft and a driven shaft, the latter affording pivotal movement to the needle by means of an extension on the driven shaft which alternately engages drive elements on a pivotal shaft which is attached to the needle. The rocker arm is driven by the driven shaft by engagement of lugs on the driven shaft and a rocker arm shaft parallel thereto.

15 Claims, 11 Drawing Figures

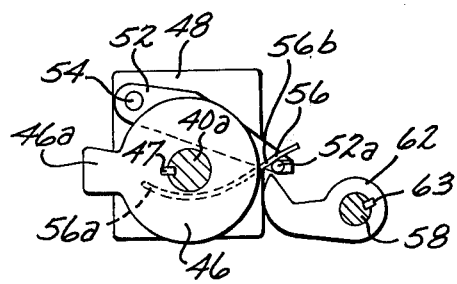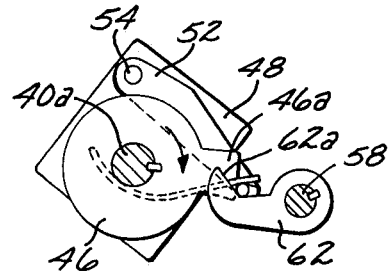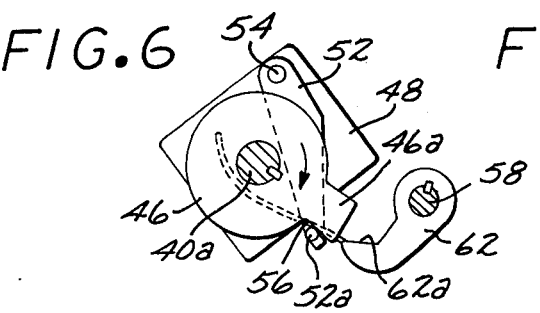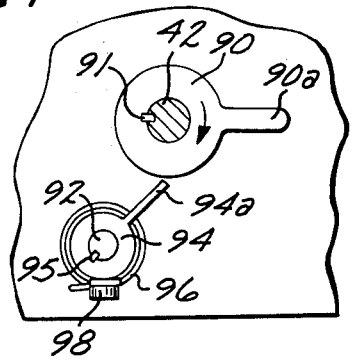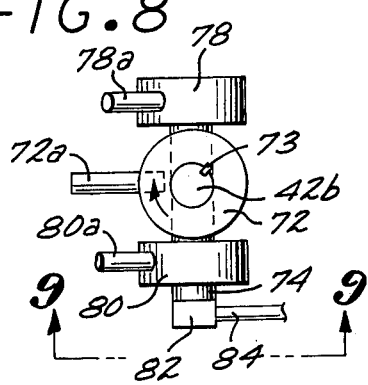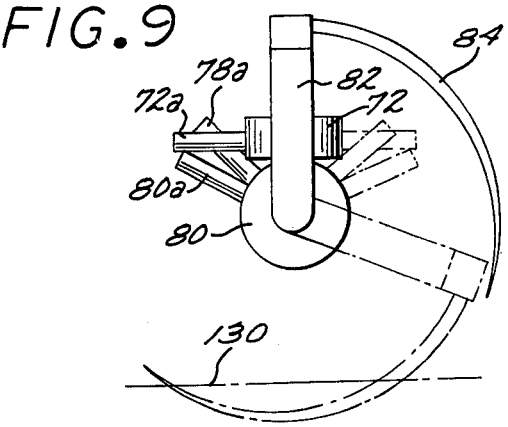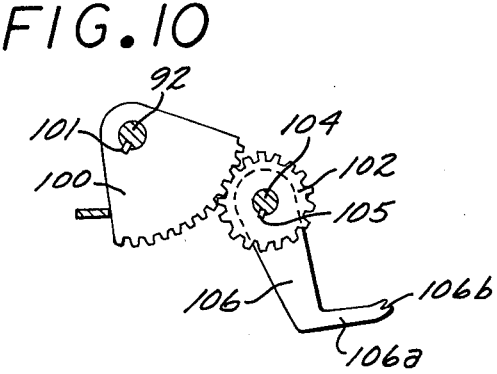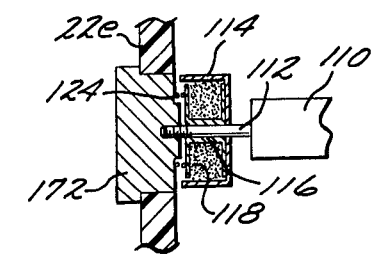

SUTURING DEVICE

The present invention relates generally to suturing devices, and more particularly to automatic devices for sewing animal skin or flesh, as for instance following a medical operation or an embalming procedure.

Considerable time and effort is spent in manually closing a wound or incision in the flesh or skin tissue of an animal. This is so whether the animal be human or not since considerable care must be taken in properly suturing such wound or incision.

Typically, a needle is employed by hand, in conjunction with suturing thread to draw the skin or flesh together at relatively small incremental spaces along the opening. Such fine work is necessary to insure that the wound heals readily and with a minimum of visible scarring. Also, the more uniformly the skin or flesh is drawn together, the more natural will be the appearance thereafter.

The time and effort consumed in closing an incision is particularly acute in the embalming industry where steps are taken to preserve the natural appearances of a body. In performing this art, relatively long incisions are required, necessitating considerable time and effort in thereafter closing such incisions.

In view of the foregoing, it is an object of the present invention to provide a suturing device which is substantially automatic for sewing relatively long openings in animal skin or flesh within a relatively short period of time.

It is another object of the present invention to provide a suturing device as characterized above which employs a continually energized motor when operating, and clutch means for substantially instantaneously commencing the performance of the suturing operation.

A further object of the present invention is to provide a suturing device as characterized above having an arcuately shaped needle which inserts the suturing thread into the flesh, and a rocker arm which intercepts the thread to form a loop for the succeeding stitch by the needle.

An even further object of the present invention is to provide a suturing device as characterized above having unique power transmission means for converting the continual rotation of a shaft in one direction into reverse pivotal movement of a shaft to which the needle is attached.

A still further object of the present invention is to provide a suturing device as characterized above whose operation can be started and stopped as desired, even though the drive motor therefor is continually operable.

An even further object of the present invention is to provide a suturing device as characterized above which is simple and inexpensive to manufacture and which is rugged and dependable in operation.

The novel featrues which I consider characteristic of my invention are set forth with particularity in the appended claims. The invention itself, however, both as to its organization and mode of operation, together with additional objects and advantages thereof, will best be understood from the following description of specific embodiments when read in connection with the accompanying drawings, in which:

FIG. 4 is a sectional view taken substantially along line 4—4 of FIG. 2 of the drawings;

FIG. 5 is a view similar to FIG. 4, but showing the parts in different positions;

Figure 2:
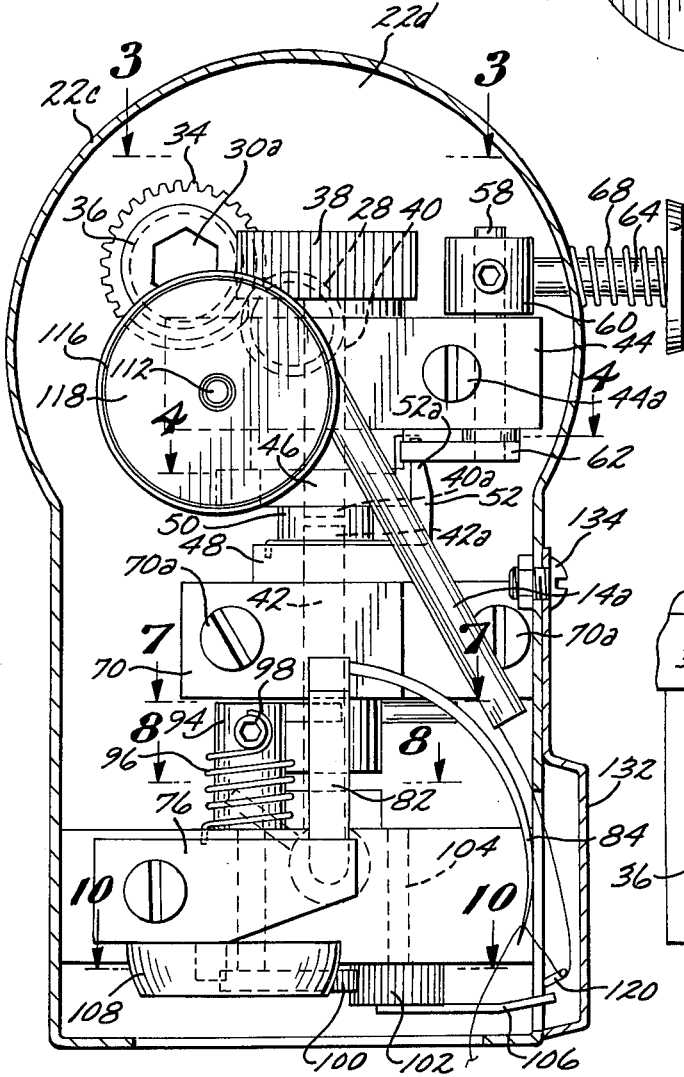
FIG. 2 is a transverse sectional view through the head of the suturing device of FIG. 1.

FIG. 6 also is a view similar to FIG. 4, but showing the parts in still another position;

FIG. 7 is a transverse sectional view taken substantially along line 7—7 of FIG. 2;

FIG. 8 is a sectional view taken substantially along line 8—8 of FIG. 2;

FIG. 9 is a side elevational view showing the drive means for the arcuate needle;

FIG. 10 is a sectional view taken substantially along line 10—10 of FIG. 2; and

Figure 1:
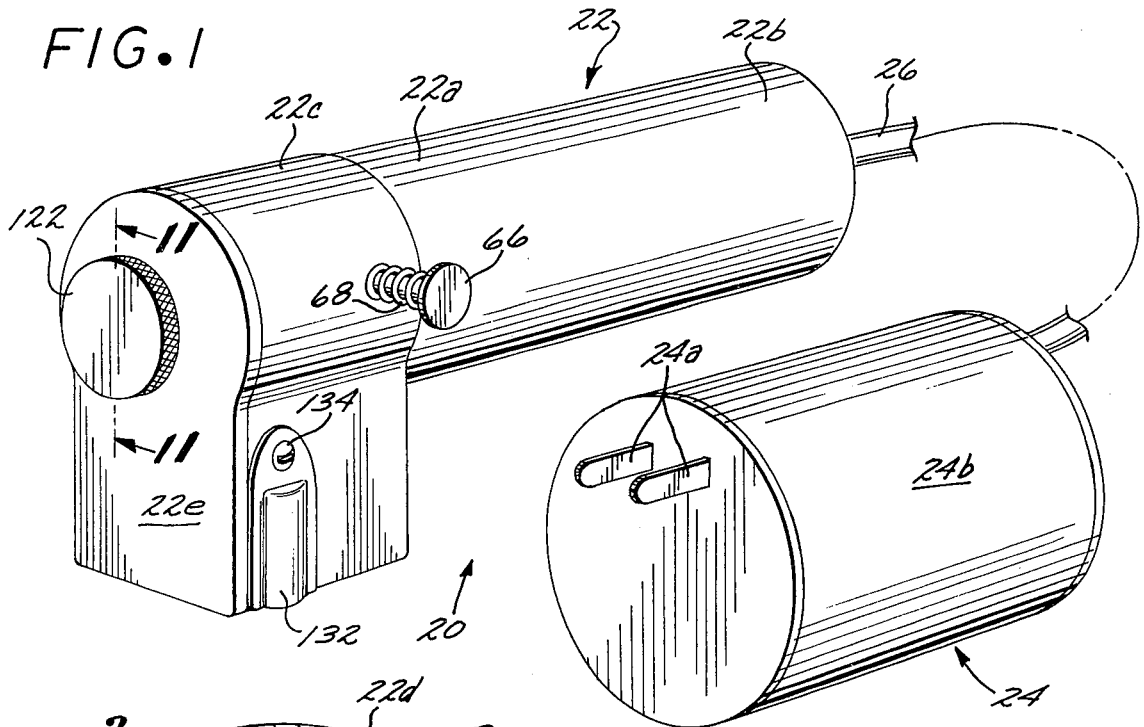
FIG. 1 is a perspective view of a suturing device according to the present invention.

FIG. 11 is a fragmentary sectional view taken substantially along line 11—11 of FIG. 1 of the drawings.

Like reference characters indicate corresponding parts throughout the several views of the drawings.

Referring to FIG. 1 of the drawings, there is shown therein a suturing device 20 comprising a main unit 22 and a transformer 24 connected together by suitable electrical wires 26. Transformer 24 is designed to be inserted into a normal household electrical outlet by means of prongs 24a. Such prongs are in circuit with a transformer unit (not shown) within the housing 24b to provide the desired electrical energy. Although not germain to the instant invention, it has been found desirable to employ 12-volt electrical power so that the transformer should be operable to reduce the usual 110-volt household power to 24-volts.

Figure 3:
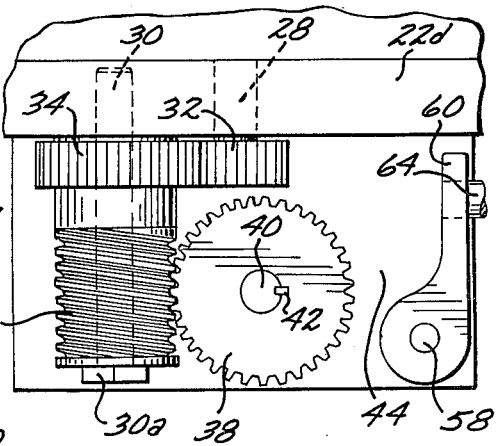
FIG. 3 is a fragmentary top view of a portion of the device, taken substantially along line 3—3 of FIG. 2.

The main unit 22 comprises a housing 22a which is divided into a motor housing 22b and a head 22c. Within housing 22b is an electrically energizable motor (not shown) which, when energized, rotates a motor shaft 28 shown in FIG. 3. Such shaft 28 extends through a partition wall 22d.

Any appropriate electrical switch means may be employed for controlling energization of the motor, as for instance an ordinary toggle switch mounted in the rear wall of the motor housing 22b.

Also mounted within partition wall 22d is a shaft 30. A drive gear 32 is secured to motor shaft 28 in engagement with a driven gear 34 which is formed integrally with a worm gear 36. Thus, rotation of motor shaft 28 causes gear 32 to drive the combination gears 34 and 36. Shaft 30 may be a bolt or the like having a bolt head as shown in the drawings.

Engageable with worm gear 36 to be driven thereby, is a gear 38 which is mounted on a drive shaft 40 by any appropriate means such as a locking key 42. As shown most particularly in FIG. 2 of the drawings, the drive shaft 40 is generally axially aligned with a driven shaft 42. The drive shaft 40 has a lower end portion 40a which is in close proximity to the upper end portion 42a of driven shaft 42.

A mounting block 44 is firmly secured to the partition wall 22d by any appropriate means such as fastening screw 44a. Such mounting block 44 is formed with a through opening for receiving the shaft 40 to enable it to rotate as will hereinafter be described.

As viewed in FIG. 2 of the drawings, the upper end of shaft 40 is provided with the aforementioned gear 38. The lower end portion 40a of shaft 40 is provided with a lug member 46 which, as shown most clearly in FIGS.

4, 5 and 6 of the drawings, is secured to shaft 40 by a locking key 47. Lug member 46 is generally circular in construction and has a radially extending lug 46a.

Mounted on the upper end portion 42a of driven shaft 42 is a member 48 which, as shown in FIGS. 4, 5 and 6, is generally square or rectangular in construction. said member 48 is firmly secured to the driven shaft 42, as is a collar 50 which is formed with a through opening for receiving the lower end portion 40a of drive shaft 40 to afford a bearing surface therefor.

Pivotally mounted on member 48, offset from the axis of rotation of the aligned shafts 40 and 42 is a catch member 52. A pivot pin 54 extends through an opening in one end of catch member 52 and is secured to member 48. For reasons which will hereinafter become more apparent, it is necessary for the pivotal axis for catch member 52 on member 48 to be offset from the axis of rotation of shaft 42.

Catch member 52 further includes a catch element 52a which is offset upwardly, as seen in FIG. 2 of the drawings. A leaf spring 56 has an end portion 56a anchored to the member 48 and its opposite end portion 56b is caused to be positioned about the catch element 52a to urge catch member 52 in a clockwise direction about its pivot pin 54, as viewed in FIGS. 4, 5 and 6 of the drawings.

Mounting block 44 is provided with another through opening for receiving a pivot pin 58. Attached to pin 58 on top of mounting block 44 is a manually operable lever 60. In similar fashion, a cam member 62 is secured to the lower end portion of shaft 58, below the mounting block 44. As shown most particularly in FIGS. 4, 5 and 6 of the drawings, the cam member 62 may be secured to pin 58 in any appropriate manner as by a locking key 63.

Said cam member 62 is formed with a cam surface 62a for cooperation with the catch element 52a of catch member 52 as will hereinafter be explained in greater detail.

The housing of the head portion 22c of main unit 22 is formed with a through opening through which a shaft or pin 64 extends. One end of shaft 64 is firmly secured to the lever 60 and the other end carries a thumb or finger button 66. A compression spring 68 is interposed betweeen the head 22c and the thumb button 66.

The driven shaft 42 is journaled within a mounting block 70, the latter being firmly secured to the partition wall 22d by appropriate fastening screws 70a. The mounting member 48 rests on top of mounting block 70.

The lower end 42b of shaft 42 carries a disc 72 wherein is mounted an extension element 72a as shown most particularly in FIG. 8 of the drawings. The disc 72 is formed with a through opening to enable it to be firmly secured to the lower end of shaft 42 by means such as fastening key 73.

Positioned beneath the lower end portion 42b of driven shaft 42 (as viewed in FIG. 2) is a rotatable driven shaft 74 which is suitably journaled in a mounting block 76 as shown most particularly in FIG. 2 of the drawings. Such shaft 74 has its pivotal axis at substantially right angles to the axis of rotation of driven shaft 42, and carries a pair of discs 78 and 80 in spaced relation, on opposite sides of the lower end portion 42b of shaft 42.

As shown most particularly in FIGS. 8 and 9 of the drawings, a mounting arm 82 is firmly secured to one end of shaft 74 to be movable therewith. Such mounting arm carries an arcuately shaped suturing needle 84 whose radius of curvature is proportional to or identical with the length of arm 82. Needles 84, for proper suturing operation, is to be reversely movable in a radial manner as depicted by the broken line representation in FIG. 9 of the drawings.

Reverse movement of needle 84 is provided by the continuous rotation of driven shaft 42. To facilitate this, each of the discs 78 and 80 is provided with an extension element 78a and 80a respectively. Such elements, it will be noted, extend radially outwardly at substantially right angles to the shaft 74. Thus, as the driven shaft 42 is caused to rotate, the extension element 72a alternately engages the extension elements 78a and 80a to provide the reverse suturing movement of needle 84. That is, with the needle in the position shown in solid lines in FIG. 9, rotation of the driven shaft 42 as shown in FIG. 8, causes the extension element 72a to engage extension element 78a and move it to the right as shown in both FIGS. 8 and 9. This causes needle 84 to be rotated to the broken line position shown in FIG. 9. Thereafter, with continued rotation of driven shaft 42 in the direction shown by the arrow in FIG. 8, the extension element 72a engages extension element 80a and moves the same from its right hand position to its left hand position, thereby returning needle 84 to its solid line position of FIG. 9.

Driven shaft 42 also carries a lug member 90, immediately beneath the mounting block 70. Such member 90, as shown most particularly in FIG. 7 of the drawings, is non-rotatably secured to shaft 42 in any appropriate manner as by a fastening or locking key 91. Member 90 is formed with a lug portion 90a.

Mounted within mounting block 76 is a pivot pin 92 which carries a lug member 94. This member may be secured to pivot pin 92 in any appropriate manner as by means of the locking key 95. Member 94 is formed with a lug portion 94a to be engaged by the lug portion 90a as will hereinafter be described. A torsion spring 96 is positioned about member 94. As shown in FIG. 2 of the drawings, spring 96 has one end offset and firmly secured to the mounting block 76. The other end is provided with a reversely bent portion which encircles a mounting screw or bolt 98. Thus, the lug member 94, as shown in FIG. 7 of the drawings, is urged by torsion spring 96 in clockwise direction.

Mounted on the lower end of pivot pin 92 is a gear segment 100, as by means of a locking key 101. Such segment cooperates with a gear 102 mounted on a shaft 104 by means of a locking key 105. Shaft 104 is mounted in block 76 and carries a rocker arm 106. Arm 106 is offset to provide an L-shape having an end portion 106a which is bifurcated as at 106b. The rocker arm 106, gear 102 and shaft 104 are a unitary structure.

The continual rotation of lug member 90 in the direction of the arrow in FIG. 7, causes the lug portion 90a to engage lug portion 94a of lug member 94. Continued movement thereof causes shaft 92 and gear segment 100 to be pivoted a predetermined angular distance. This causes rocker arm 106 to be moved in a clockwise direction as viewed in FIG. 9, through gear member 102 and pin 104. Upon disengagement of the lug portions 90a and 94a, torsion spring 96 returns rocker arm 106 to the position shown in FIG. 10, through the aforementioned gear segment 100 and gear member 102.

A guard 108 formed of sheet metal is attached to the mounting block 76 to properly shield the gear segment 100.

As shown in FIG. 11 of the drawings, an extension 110 is provided on mounting block 44 and a threaded stud 112 is secured to such extension. A bobbin holder 114 formed of sheet metal or the like is mounted on the stud 112 and is provided with an elongated outlet member 14a. The bobbin holder 14 is generally cup shaped, having a round periphery to accept and retain a bobbin 116 whereon suture thread 118 is wound. As shown most particularly in FIG. 2 of the drawings, the suture thread is extended down through the elongated outlet 114a and is wrapped about a stationary post 120 attached to the cover of head 22c. The thread, as shown, is then threaded through a hole in the end of the needle 84.

The enclosure for head 22c further comprises an access plate 22e which can be removed to afford access to the various components of the suturing device. A retaining knob 122 of generally circular configuration is provided in the access plate 22e to threadedly engage the end of stud 112. Such knob retains the bobbin assembly in proper position for feeding suturing thread to the needle 84. A compression spring 124 may be interposed between the knob and the bobbin 116 to retain the bobbin in place.

The suturing device operates generally as follows. The transformer unit 24 is inserted into a normal 110-volt outlet. Actuating the on/off switch (not shown) to the "on" position causes the motor (also now shown) to operate continually.

Such operation of the motor causes drive shaft 40 to rotate continually, through gears 32, 34, 36 and 38. As a result, lug member 46 rotates in the direction shown by the arrows in FIGS. 4, 5 and 6.

With the catch member 52 biased to its normal position by leaf spring 56, the catch element 52a is in its position closest to the axis of rotation of drive shaft 40. Thus, when lug 46a engages catch element 52a, the motion from drive shaft 40 is transmitted through lug 46a to catch element 52a so as to commence rotation of drive shaft 42.

However, with cam member 62 is the position shown in FIG. 4 of the drawings, the catch element 52a is caused to ride along cam surface 62a until the position shown in FIG. 5 is reached, whereupon lug 46a is disengaged from catch element 52a. Thus, the clutch arrangement between the drive shaft 40 and driven shaft 42 operates to prevent the transmission of power therebetween, and the suturing apparatus driven by shaft 42 cannot operate.

When it is desired to operate the suturing apparatus, it is merely necessary to manually depress the thumb button 66 against the force of compression spring 68. This causes the shaft 58 to pivot sufficiently to move cam member 62 out of possible interference with catch element 52a. Upon the next rotation of lug 46, the catch element 52a is engaged and retained by the lug as shown in FIG. 6, thus causing the dirve shaft 40 to rotate driven shaft 42.

When this occurs, the needle with suturing thread attached thereto is caused to move back and forth as depicted in FIG. 9, by virtue of the aforedescribed alternate engagment of the extension element 72a with the extension elements 78a and 80a.

Simultaneous therewith, the lug extension 90a engages the lug extension 94a to pivot gear segment 100, and subsequently the torsion spring 96 is effective to return such segment to its original position. Such back and forth movement of gear segment 100 causes the rocker arm 106 to move back and forth accordingly.

The forward motion of needle 84 takes the thread through the skin, as represented by the dotted line 130 in FIG. 9, and exposes the same above the surface of the skin. At this point, the rocker arm bifurcated end 106b is in its retracted position to engage the thread, and following return movement of needle 84, the rocker arm 106 carries the thread back toward the original position of the needle as shown in solid lines in FIG. 9.

The needle 84 then moves forward again, this time being inserted in the loop afforded by the thread held by the bifurcated end 106b, and as soon as this is accomplished, the rocker arm 106 returns to its retracted position.

This suturing operation continues until the thumb button 66 is released. At this time, the aforedescribed clutch assembly as shown in FIGS. 4 and 5 prevents power from being transmitted from shaft 40 to shaft 42.

For purposes of threading the needle, a small access plate 132 is pivotally mounted on the side of the enclosure for head 22c by means of a fastening nut 134.

It is contemplated within the present invention that various different types or styles of head 22c may be substituted for the one shown in the drawings. Such heads can be interchangeable and can provide different length or type of stitch provided by the subject suturing device.

It is thus seen that the present invention provides a suturing device which is capable of automatically sewing animal skin or flesh. Although I have shown and described certain specific embodiments of my invention, I am well aware that many modifications thereof are possible. The invention, accordingly, is not to be restricted except insofar as is necessitated by the prior art and by the appended claims.

I claim:
1. A suturing device comprising in combination,
   a housing,
   a motor in said housing having a rotatable drive shaft,
   suturing apparatus including a movably mounted suturing needle and a source of suturing thread therefor, and a rotatably mounted driven shaft for moving said needle,
   and clutch means interposed between said drive and driven shafts comprising a continually rotating lug on said drive shaft and a catch member movably mounted relative to said driven shaft and biased into a position to be engaged by said lug,
   said clutch means further including a cam member movably mounted relative to said housing and having a cam surface normally positioned to move said catch member against its bias to position it out of said first mentioned position for engagement by said lug to thereby prevent rotation of said driven shaft by said drive shaft,
   said cam member being movable to a position where said cam surface is prevented from overcoming said bias and disengaging said catch member from said lug to thereby permit said lug to engage said catch member and effect rotation of said driven shaft by said drive shaft.
2. A suturing device according to claim 1,
   wherein said catch member is pivotally mounted relative to said driven shaft.

3. A suturing device according to claim 2, wherein said drive and driven shafts are generally axially aligned and said catch member is formed with a catch element, said member being biased to a position where said element is relatively close to the axis of rotation of said shaft to thereby be engaged by said lug, said cam surface being operable in its normal position to move the catch element of said catch member away from said axis to effect disengagement of said lug and said catch element.

4. A suturing device according to claim 3, wherein said clutch means further includes an extension on said driven shaft and said catch member is pivotally mounted on said extension on an axis spaced from the axis of rotation of said driven shaft.

5. A suturing device according to claim 4, wherein said lug is of predetermined length to have a predetermined maximum circumference of rotation with said drive shaft and said catch member is pivotally biased to a position of said catch element within said predetermined circumference of rotation to be engaged by said lug, said cam surface being operable when said cam member is in its normal position to intercept said catch element following engagement by said lug to move said catch member against its said bias to thereby move said catch element outside said circumference of rotation to prevent rotation of said driven shaft by said drive shaft.

6. A suturing device comprising in combination,
a housing,
a motor in said housing having a rotatable drive shaft,
suturing apparatus including a reversely movable suturing needle and a source of suturing thread therefor,
a reversely pivotal shaft having connection with said needle such that reverse pivotal movement thereof effects reverse movement of said needle,
a pair of spaced drive elements attached to and extending from said pivotal shaft in generally parallel relation to each other,
and a rotatable driven shaft to be connected to said drive shaft and mounted at an angle to said pivotal shaft and between said drive elements, said driven shaft having an extension thereon for engagement alternatively with said drive elements, whereby as the driven shaft is rotated in one direction said extension alternately engages said drive elements to effect reverse pivotal movement of said pivotal shaft.

7. A suturing device according to claim 6, wherein said driven shaft has an end portion substantially equidistant between said drive elements.

8. A suturing device according to claim 7, wherein said driven shaft is positioned at approximately right angles to said pivotal shaft and said drive elements are at substantially right angles to said pivotal shaft and said extension is at substantially right angles to said driven shaft.

9. A suturing device according to claim 8, wherein said needle is arcuately shaped and an arm is provided for attaching said needle to said pivotal shaft, whereby reverse pivotal movement of said pivotal shaft causes said needle to move forward and backward along its arcuate shape.

10. A suturing device according to claim 6, wherein a rocker arm is pivotally mounted relative to said housing and is driven by said driven shaft to intercept the suture thread following insertion thereof by said needle to provide a loop for the succeeding stitch by said needle.

11. A suturing device according to claim 10, wherein said rocker arm is formed with a bifurcated end portion for intercepting said thread.

12. A suturing device according to claim 11, wherein said rocker arm is connected to a pivotal member biased in a given direction, therebeing engageable lugds on said driven shaft and said pivotal member to move said rocker arm from a first position to a second position against the bias of said pivotal member.

13. A suturing device comprising in combination,
a housing,
a motor in said housing having a rotatable drive shaft,
suturing apparatus including a movably mounted suturing needle and a source of suturing thread therefor,
a rotatably mounted driven shaft interposed between said drive shaft and said suturing apparatus,
clutch means interposed between said drive and driven shafts comprising a continually rotating lug on said drive shaft and a catch member movably mounted relative to said driven shaft engageable by said lug,
said clutch means further including a cam member movably mounted relative to said housing and having a cam surface normally positioned to disengage said catch member from said lug to prevent rotation of said driven shaft by said drive shaft, said cam member being movable to a position where said cam surface is prevented from disengaging said catch member from said lug to permit rotation of said driven shaft by said drive shaft,
a reversely pivotal shaft having connection with said needle such that reverse pivotal movement of said pivotal shaft effects reverse movement of said needle,
a pair of spaced drive elements attached to and extending from said pivotal shaft in generally parallel relation,
and an extension formed on said driven shaft for engaging said drive elements alternately as said driven shaft is continually rotated in the same direction to thereby afford reverse movement of said needle.

14. A suturing device according to claim 13, wherein a rocker arm is pivotally mounted relative to said housing and is driven by said driven shaft to intercept the suture thread following insertion thereof by said needle to provide a loop for the succeeding stitch by said needle.

15. A suturing device according to claim 1, wherein a rocker arm is pivotally mounted relative to said housing and is driven by said driven shaft to intercept the suture thread following insertion thereof by said needle to provide a loop for the succeeding stitch by said needle.

* * * * *